US012778437B2

(12) United States Patent
Shah et al.

(10) Patent No.: US 12,778,437 B2
(45) Date of Patent: Nov. 3, 2026

(54) OBTAINING BLOOD PRESSURE MEASUREMENTS

(71) Applicant: Meta Platforms Technologies, LLC, Menlo Park, CA (US)

(72) Inventors: Rashmee Shah, Salt Lake City, UT (US); Myriam Amsallem, San Francisco, CA (US); Kevin Kai-Feng Chiou, Hawthorn Woods, IL (US); Teodora Sandra Buda, Barcelona (ES)

(73) Assignee: Meta Platforms Technologies, LLC, Menlo Park, CA (US)

( * ) Notice: Subject to any disclaimer, the term of this patent is extended or adjusted under 35 U.S.C. 154(b) by 283 days.

(21) Appl. No.: 18/537,541

(22) Filed: Dec. 12, 2023

(65) Prior Publication Data

US 2024/0225459 A1 Jul. 11, 2024

Related U.S. Application Data

(60) Provisional application No. 63/479,069, filed on Jan. 9, 2023.

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02416* (2013.01); *A61B 5/1126* (2013.01);
(Continued)

(58) Field of Classification Search
CPC ... A61B 5/022; A61B 5/02416; A61B 5/1126; A61B 5/397; A61B 5/742; A61B 5/7475;
(Continued)

(56) References Cited

U.S. PATENT DOCUMENTS 7,544,168 B2 6/2009 Nitzan
10,045,700 B2 8/2018 Noh et al.
(Continued)

FOREIGN PATENT DOCUMENTS

DE 102019101353 A1 * 1/2020 ............ A61B 5/022
WO WO-2021241925 A1 12/2021
(Continued)

OTHER PUBLICATIONS

European Search Report for European Patent Application No. 24150883.7, dated May 24, 2024, 3 pages.
(Continued)

*Primary Examiner* — Brian L Casler
(74) *Attorney, Agent, or Firm* — Morgan, Lewis & Bockius LLP

(57) ABSTRACT

Methods, systems, and media for determining blood pressure measurements are provided. In some embodiments, a method for determining blood pressure measurements comprises: obtaining a set of photoplethysmography (PPG) signals using a wearable device worn by a user; determining that a blood pressure of the user is being measured by a device unassociated with the wearable device based at least in part on the set of PPG signals; responsive to determining that the blood pressure of the user is being measured by the device unassociated with the wearable device, obtaining an indication of a blood pressure measurement obtained by the device unassociated with the wearable device; and storing the obtained indication of the blood pressure measurement for future use by the wearable device.

20 Claims, 6 Drawing Sheets

(51) Int. Cl.
*A61B 5/024* (2006.01)
*A61B 5/11* (2006.01)
*A61B 5/397* (2021.01)

(52) U.S. Cl.
CPC .............. *A61B 5/397* (2021.01); *A61B 5/742* (2013.01); *A61B 5/7475* (2013.01)

(58) Field of Classification Search
CPC ............ A61B 2560/0223; A61B 5/681; A61B 5/02116; A61B 5/746; A61B 5/1118; A61B 5/6824; A61B 5/313; A61B 5/021; A61B 5/02208; A61B 5/02216; A61B 5/02438; G16H 10/60; G16H 50/30
USPC .......................................................... 600/485
See application file for complete search history.

(56) References Cited

U.S. PATENT DOCUMENTS 11,219,375 B2 1/2022 Lee et al.
2014/0172310 A1* 6/2014 Chin ....................... G16Z 99/00 702/19
2015/0363561 A1* 12/2015 Watson .................. G16H 50/20 702/19
2016/0045119 A1 2/2016 David et al.
2016/0198963 A1* 7/2016 Addison .............. A61B 5/7221 600/480
2018/0098731 A1 4/2018 Yoon et al.

FOREIGN PATENT DOCUMENTS

WO WO-2022146881 A1 7/2022
WO WO-2022179351 A1 9/2022

OTHER PUBLICATIONS

Nitzan M., et al., "Automatic Noninvasive Measurement of Systolic Blood Pressure using Photoplethysmography," BioMedical Engineering OnLine, Oct. 26, 2009, vol. 8, No. 28, 8 pages.

* cited by examiner

OBTAINING BLOOD PRESSURE MEASUREMENTS

CROSS-REFERENCE TO RELATED APPLICATIONS

This application claims priority under 35 U.S.C. § 119 to U.S. Provisional Application No. 63/479,069, filed on Jan. 9, 2023, the contents of which are hereby incorporated by reference in their entirety for all purposes.

BACKGROUND

Accurate and non-invasive blood pressure measurements may be important, for example, to monitor cardiovascular heath, quickly identify blood pressure abnormalities that may portend a serious health issue, etc. Because blood pressure can vary substantially over the course of the day, quick and accurate measurements of blood pressure may be useful to allow people to monitor and track their health. However, accurate measurements of blood pressure, that are measured quickly and non-invasively, are difficult to obtain.

SUMMARY

Disclosed herein are techniques for obtaining blood pressure measurements. In some embodiments, a method involves obtaining a set of photoplethysmography (PPG) signals using a wearable device worn by a user; determining that a blood pressure of the user is being measured by a device unassociated with the wearable device based at least in part on the set of PPG signals; responsive to determining that the blood pressure of the user is being measured by the device unassociated with the wearable device, obtaining an indication of a blood pressure measurement obtained by the device unassociated with the wearable device; and storing the obtained indication of the blood pressure measurement for future use by the wearable device.

In some embodiments, a wearable device comprises at least one light emitter and at least one light detector; and a controller. The controller may be configured to: obtain a set of photoplethysmography (PPG) signals using the at least one light emitter and at least one light detector; determine that a blood pressure of a user wearing the wearable device is being measured by a device unassociated with the wearable device based at least in part on the set of PPG signals; responsive to determining that the blood pressure of the user is being measured by the device unassociated with the wearable device, obtain an indication of a blood pressure measurement obtained by the device unassociated with the wearable device; and store the obtained indication of the blood pressure measurement for future use by the wearable device.

In some embodiments, a method involves obtaining a set of photoplethysmography (PPG) signals using a wearable device worn by a user; determining that a blood pressure of the user is being measured by another device, based at least in part on the set of PPG signals and without communicating any data to or from the other device; responsive to determining that the blood pressure of the user is being measured by the another device, obtaining an indication of a blood pressure measurement obtained by the another device; and storing the obtained indication of the blood pressure measurement for future use by the wearable device.

BRIEF DESCRIPTION OF THE DRAWINGS

Illustrative embodiments are described in detail below with reference to the following figures.

Figure 1:
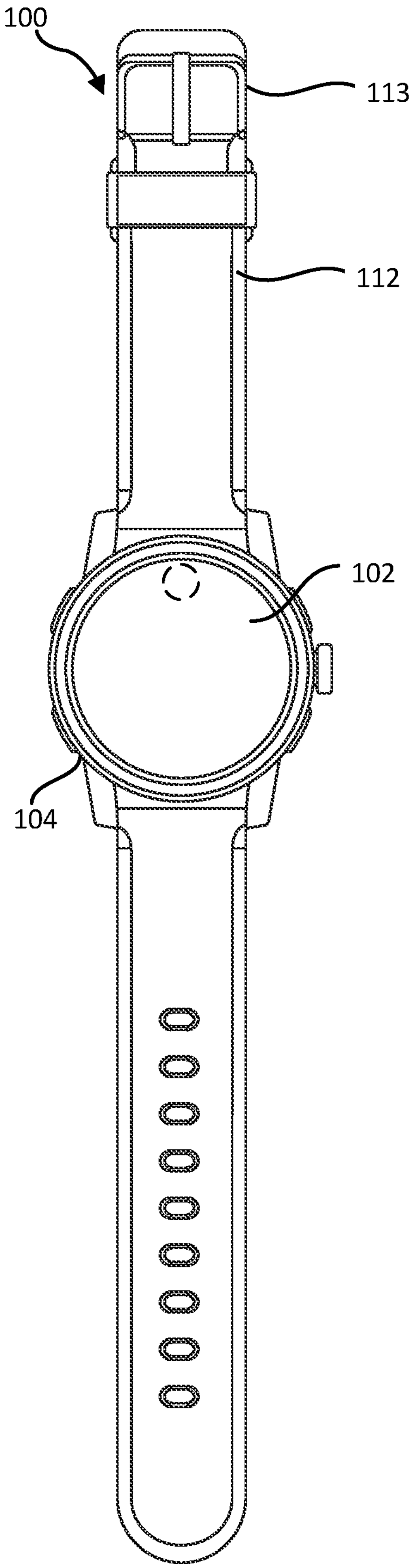
FIG. 1 is a plan view of an example wristband system in accordance with some embodiments.

The figures depict embodiments of the present disclosure for purposes of illustration only. One skilled in the art will readily recognize from the following description that alternative embodiments of the structures and methods illustrated may be employed without departing from the principles, or benefits touted, of this disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Blood pressure is a physiological characteristic that users may want to monitor regularly, e.g., to track changes in health and/or to monitor for serious health complications. Accurate detection of blood pressure using a non-invasive and non-obtrusive wearable device is desired. Such a wearable device would enable continuous and unobtrusive monitoring of blood pressure as a wearer of the device goes about their day, e.g., during various activities, during sleep, etc. However, accurate blood pressure determination using such a wearable device is difficult to achieve. In particular, while various techniques have been studied for determining blood pressure using a wearable device, such techniques typically determine a relative blood pressure that then need to be scaled to an absolute blood pressure. In other words, a relative blood pressure may be useful to indicate changes in blood pressure for a given person, but need to be scaled to indicate an absolute blood pressure that is, e.g., comparable to that measured in a doctor's office or other clinical setting. For example, such relative blood pressures may be determined using photoplethysmography (PPG), where a light is emitted from a light emitter disposed in the wearable device toward skin of the wearer, and reflected light is captured by a light detector and characterized to form a PPG signal. Various techniques may be applied to the PPG signal to determine a relative blood pressure. However, to generate an absolute blood pressure from a relative blood pressure (e.g., as would be obtained using an oscillometric technique as performed at a doctor's office using a blood pressure cuff), a calibration must be performed to transform the relative blood pressure to an absolute blood pressure. Conventional techniques may require the user to obtain an absolute blood pressure for calibration of future relative blood pressure measurements, where the absolute blood pressure is obtained using a standard blood pressure cuff. In other words, in order to transform relative blood pressure measurements obtained by a wearable device, conventional techniques require a calibration procedure to be performed using a blood pressure cuff or other obtrusive method. Moreover, this calibration procedure may need to be repeated periodically (e.g., every month, every two weeks, etc.) in order to account for drift to re-calibrate relative blood pressure measurements.

Disclosed herein are methods, systems, media, and techniques for obtaining an absolute blood pressure measurement that may be used to calibrate relative blood pressure measurements obtained by a wearable device. The wearable device may be a smart watch (e.g., as shown in and described below in connection with FIG. 1), a fitness tracker, smart glasses, an AR/VR headset, or the like. As described below in connection with FIG. 2, the wearable device may detect that a user's blood pressure is being measured by a device unassociated with the wearable device. For example, the unassociated device may be a device for measuring a user's blood pressure in a clinical setting, such as a sphygmomanometer, an oscillometric cuff, or the like. It should be noted that, as used herein, an "unassociated device" refers to a device that is not communicatively coupled (e.g., by way of a wired or wireless communication channel) to a device owned by and/or carried by the user. In some cases, an "unassociated device" may be one that is itself not owned by the user and/or carried by the user. Examples of devices owned by and/or carried by the user include the wearable device, a mobile device (e.g., a mobile phone or a tablet computer) paired with the wearable device, or the like. In one example, the unassociated device may be a blood pressure cuff device (e.g., that utilizes the oscillometric technique, or any other technique) in a clinical setting such as a doctor's office or a pharmacy. In particular, the unassociated device in this example may be considered "unassociated" with the wearable device because the unassociated device is not in communication with the wearable device or a mobile device paired with the wearable device. Additionally, the blood pressure cuff device is not owned by and/or carried by a wearer of the wearable device. Note that, even though the blood pressure cuff device may be communicatively coupled to a medical records server, and the wearable device and/or a mobile device paired with the wearable device may be configured to access the medical records server, the blood pressure cuff device in this example may be considered an "unassociated device" due to no direct communication channel between the blood pressure cuff device and any device owned by or carried by the user. In contrast, a mobile device paired with the wearable device is not considered "an unassociated device," due to being communicatively coupled with the wearable device. As another example, a blood pressure cuff device that is paired with or coupled with a mobile device (e.g., via a USB port or a LIGHTNING port) owned by or carried by the user, that is in turn paired with the wearable device is not considered "an unassociated device" due to being communicatively coupled with the mobile device that is paired with the wearable device.

In some implementations, the wearable device may detect that the user's blood pressure is being measured based on PPG signals that are obtained by the wearable device. For example, the wearable device may determine, based on the PPG signals, that blood pressure is being detected by detecting a signature in the PPG signals that characterizes occlusion of an arterial blood vessel, e.g., due to a blood pressure cuff associated with the unassociated device being inflated.

In some implementations, responsive to detecting that the user's blood pressure is being measured by the unassociated device, the wearable device may cause the blood pressure measurement (e.g., as measured by the unassociated device) to be obtained. For example, the wearable device (or a mobile device paired with the wearable device) may cause a user interface to be presented that requests that the user input the blood pressure measurement. As another example, the wearable device and/or a mobile device paired with the wearable device may cause a query to be transmitted to a medical records server that requests the blood pressure measurement made by the unassociated device. Techniques for obtaining the blood pressure measurement are shown in and described below in connection with FIGS. 3 and 4.

An example of a wearable user device that may include sensing electrodes is a wrist-worn device, such as a smart watch or fitness tracker. FIG. 1 illustrates an example wristband system 100 that includes a watch body 104 coupled to a watch band 112. Watch body 104 and watch band 112 may have any size and/or shape that is configured to allow a user to wear wristband system 100 on a body part (e.g., a wrist). Wristband system 100 may include a retaining mechanism 113 (e.g., a buckle) for securing watch band 112 to the user's wrist. Information, such as the time, date, measured user characteristics (e.g., physiological characteristics), etc. may be displayed on display 102. Display 102 may be a touchscreen such that the user may navigate through, e.g., menus, by touching portions of display 102. Wristband system 100 may perform various functions associated with the user. The functions may be executed independently in watch body 104, independently in watch band 112, and/or in communication between watch body 104 and watch band 112. Watch band 112 may be configured to operate independently (e.g., execute functions independently) from watch body 104. Additionally or alternatively, watch body 104 may be configured to operate independently (e.g., execute functions independently) from watch band 112. In some implementations, watch band 112 and/or watch body 104 may each include the independent resources required to independently execute functions. For example, watch band 112 and/or watch body 104 may each include a power source (e.g., a battery), a memory, data storage, a processor (e.g., a CPU), communications, a light source (e.g., at least one infrared LED for tracking watch body 104 and/or watch band 112 in space with an external sensor), and/or input/output devices. In some implementations, EMG electrodes for sensing EMG signals may be disposed in and/or on a portion of wristband system 100 that is configured to be in contact with the user's skin. For example, electrodes may be disposed on a back portion of watch band 112, a back portion of watch body 104, or any combination thereof.

In some implementations, a wearable device (e.g., a smart watch, a fitness tracker, etc.) may detect that a blood pressure is being measured by an unassociated device. The unassociated device may be a blood pressure measuring device (e.g., a cuff-based oscillometric device, a sphygmomanometer, etc.) that is, e.g., used in a clinical setting such as a doctor's office, a pharmacy etc. The unassociated device may be one that is unassociated with the wearable device by, e.g., not being in communication with a device owned by and/or carried by the wearer of the wearable device. For example, the unassociated device may be unassociated due to not being in communication with the wearable device, a mobile phone paired with the wearable device, etc. The wearable device may detect that the blood pressure is being measured by the unassociated device based on PPG signals obtained by the wearable device. For example, the wearable device may detect that blood pressure is being measured based on a characteristic of the PPG signals, such as that an amplitude or amplitude of an envelope of the PPG signals is below a predetermined threshold, that the amplitude or the amplitude of an envelope of the PPG signals changes in a manner that satisfies criteria indicative of blood pressure being measured, etc. The PPG signals may indicate that arterial blood flow is being restricted or occluded by at least a portion of the unassociated device, such as by a blood pressure cuff. Responsive to detecting that blood pressure is being measured, an indication of the blood pressure may be obtained (e.g., via a user interface prompt, via a query to a medical records server, or the like).

Figure 2:
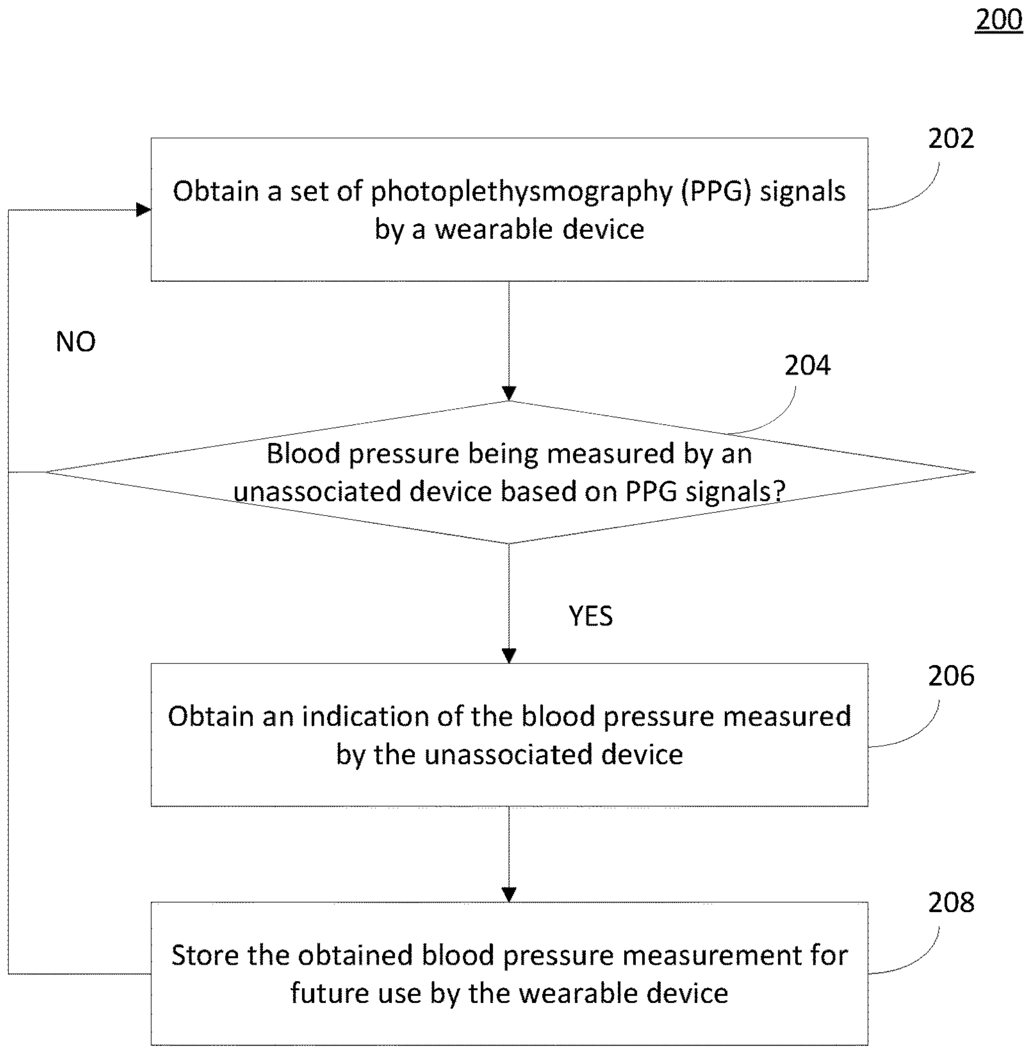
FIG. 2 is a flowchart of an example process for obtaining and storing an indication of a blood pressure measurement by a wearable device in accordance with some embodiments.

FIG. 2 is a flowchart of an example process 200 for obtaining blood pressure measurements in accordance with some embodiments. In some embodiments, blocks of process 200 may be executed by a processor or a controller of a wearable device. In some implementations, blocks of process 200 may be executed in an order other than what is shown in FIG. 2. In some embodiments, two or more blocks of process 200 may be executed substantially in parallel. In some embodiments, one or more blocks of process 200 may be omitted.

Process 200 can begin at 202 by obtaining a set of PPG signals by a wearable device. The PPG signals may be obtained using, e.g., at least one light emitter configured to emit light toward skin of the wearer, and at least one light detector configured to capture light reflected from skin and body portions of the wearer. The wearable device may include a processor configured to characterize reflected light to generate the PPG signals. The light may be emitted toward a wrist of the wearer, toward a fingertip of the wearer, toward an ear lobe of the wearer, and/or any other suitable body region.

At 204, process 200 can determine whether blood pressure is being measured by an unassociated device based on the PPG signals. As described above, the unassociated device may be a blood pressure measuring device in, e.g., a clinical setting (e.g., a doctor's office, a pharmacy, etc.). Process 200 may determine whether blood pressure is being measured based on whether the PPG signals satisfy criteria indicative of blood pressure being measured. In some implementations, the criteria may include whether the amplitude of the PPG signals or the amplitude of the envelope of the PPG signals satisfy particular amplitude criteria. The amplitude criteria may include the amplitude or the amplitude of the envelope being below a predetermined threshold. The amplitude criteria may include the amplitude or the amplitude of the envelope decreasing over a period of time (e.g., over one second, over two seconds, over five seconds, over ten seconds, etc.). The amplitude criteria may include the amplitude or the amplitude of the envelope decreasing over a period of time then subsequently increasing over a period of time. Changes in the amplitude and/or the amplitude of the envelope may be reflective of blood in arterial vessels being occluded, e.g., by a blood pressure cuff of the unassociated device. By way of example, in an instance in which the wearer is having their blood pressure measured (e.g., in a doctor's office) by a device that inflates a cuff then deflates a blood pressure cuff around their arm, the PPG signals may indicate, e.g., that blood flow is occluded as the cuff is inflated, then allowed to resume normal blood flow as the cuff is deflated.

In some implementations, process 200 may utilize the PPG signals in conjunction with other signals (e.g., sensor data) to determine if blood pressure is being measured. For example, in some implementations, process 200 may utilize various signals to determine or predict a likely arm position of the wearer. In such instances, the signals may be obtained from motion sensors (e.g., accelerometers, gyroscopes, magnetometers, etc.) and/or EMG electrodes disposed in or on the wearable device. In some implementations, process 200 may utilize an arm position of the user to verify that blood pressure is being measured. For example, in an instance in which the PPG signals indicate that blood pressure is being measured but the arm position indicates the user's arm is in a position unconventional for measuring blood pressure (e.g., raised over their head, twisted behind their back, etc.), process 200 may determine that blood pressure is not being measured based on the arm position. Conversely, in instances in which the PPG signals indicate that blood pressure is being measured and the arm position indicates that the user's arm is in a position conventional for measuring blood pressure (e.g., relatively flat and/or horizontal to the ground), process 200 may determine that blood pressure is being measured, e.g., by utilizing the arm position as a confirmation signal.

If, at 204, process 200 determines that blood pressure is not being measured ("no" at 204), process 200 can loop back to block 202 and can obtain another set of PPG signals by the wearable device.

Conversely, if, at 204, process 200 determines that blood pressure is being measured ("yes" at 204), process 200 can proceed to block 206 and can obtain an indication of the blood pressure measured by the unassociated device. In some implementations, the indication of the blood pressure measurement may be obtained by causing a user interface to be presented, where the user interface prompts the user to enter in the measured blood pressure. Additionally or alternatively, in some embodiments, the indication of the blood pressure measurement may be obtained by causing a query to be transmitted to a medical records server, where the server transmits, responsive to the query, the indication of the blood pressure measurement. Example techniques for obtaining the indication of the blood pressure measurement are shown in and described below in connection with FIGS. 3 and 4.

At 208, process 200 can store the obtained blood pressure measurement for future use by the wearable device. For example, in some implementations, the obtained blood pressure measurement may be utilized as an absolute blood pressure that is used to calibrate relative blood pressure measurements obtained using the wearable device (e.g., using PPG signals, and/or any other suitable technique).

Process 200 may then loop back to block 202. In some implementations, process 200 may loop through 202-208 to identify timepoints at which the user may be having their blood pressure measured. At each time block 208 is executed, the stored blood pressure may be updated using the indication of the blood pressure measurement, e.g., to update the absolute blood pressure value utilized by the wearable device to calibrate relative blood pressure measurements.

In some implementations, responsive to determining that a blood pressure is being measured (e.g., by a clinical cuff-based measurement device in a clinical setting, such as a doctor's office or a pharmacy), the blood pressure measurement may be obtained. In some embodiments, the blood pressure may be obtained via explicit user input. For example, a user interface may be presented, where the user interface is configured to receive user input specifying the blood pressure as measured. Additionally or alternatively, in some embodiments, the blood pressure measurement may be obtained without explicit user input. For example, in some embodiments, the blood pressure measurement may be obtained by causing a query to be transmitted to a medical records server configured to receive and store the blood pressure measurement. The medical records server may be communicatively coupled to the unassociated device that measures the blood pressure such that the blood pressure measurement is automatically stored in the medical records server upon measurement. In some embodiments, the query may include timing information to enable accurate identification of the medical record that includes the blood pressure measurement. For example, the timing information may include a date and/or a timestamp associated with the time the determination that blood pressure is being measured was made by the wearable device and/or a date and/or a timestamp associated with the obtained PPG signals used to determine blood pressure was being measured.

Figure 3:
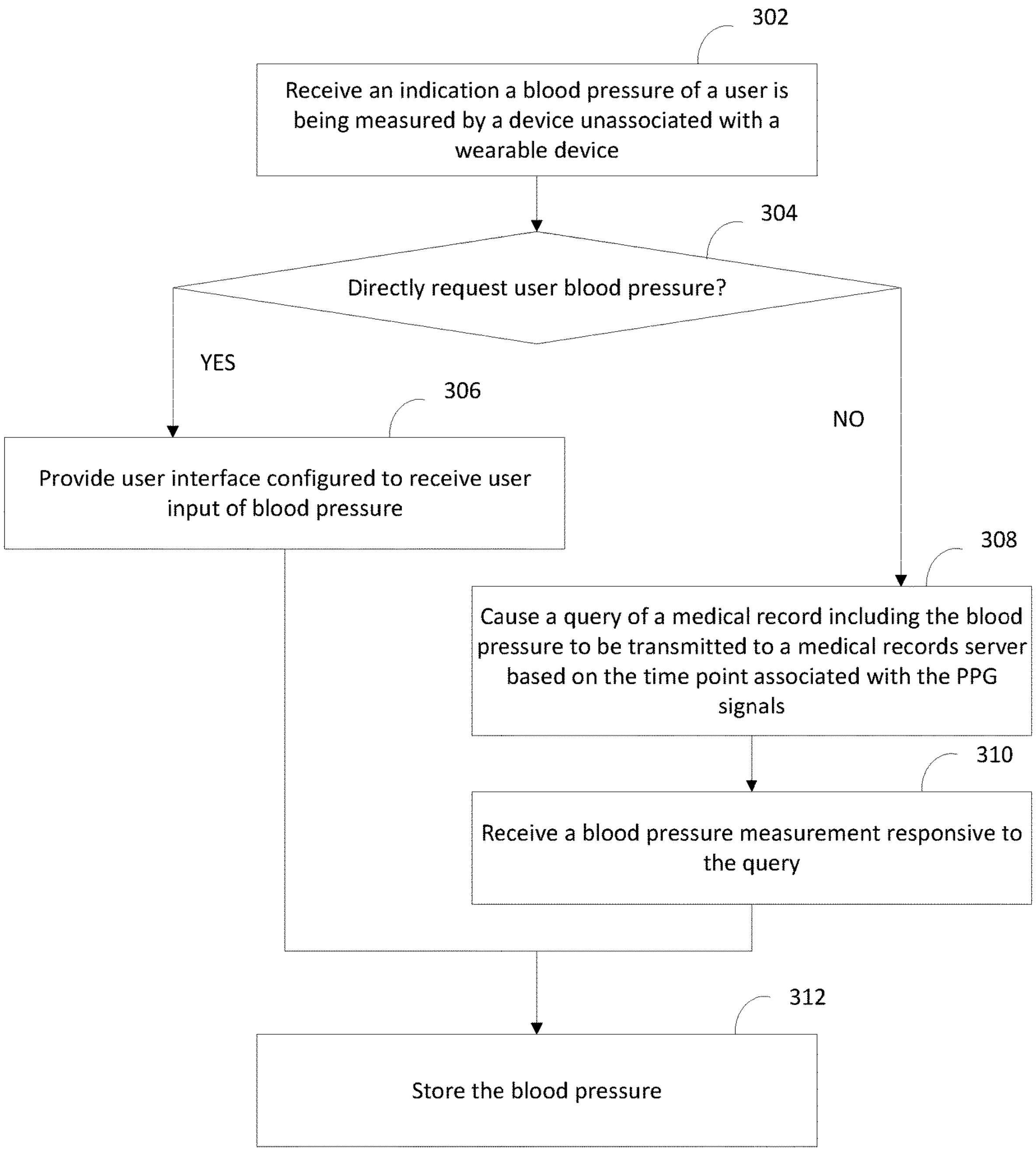
FIG. 3 is a flowchart of an example process for obtaining an indication of a blood pressure measurement in accordance with some embodiments.

FIG. 3 is a flowchart of an example process 300 for obtaining a blood pressure measurement obtained by a device unassociated with a wearable device in accordance with some embodiments. In some implementations, blocks of process 300 may be executed by a wearable device (e.g., a wearable device configured to detect that blood pressure is being measured by the unassociated device) and/or a mobile device paired with the wearable device. The mobile device may be, e.g., a mobile phone, a tablet computer, or the like. In some implementations, blocks of process 300 may be executed in an order other than what is shown in FIG. 3. In some embodiments, two or more blocks of process 300 may be executed in an order other than what is shown in FIG. 3. In some embodiments, one or more blocks of process 300 may be omitted.

Process 300 can begin at 302 by receiving an indication a blood pressure of a user is being measured by a device unassociated with a wearable device being worn by the user. For example, the unassociated device may be a sphygmomanometer or cuff-based oscillometric device. The indication the blood pressure is being measured may be, e.g., a result of block 204 of FIG. 2, as described above.

At 304, process 300 can determine whether the blood pressure measurement is to be directly requested. In some implementations, process 300 may determine whether to directly request (e.g., via user interface) the blood pressure based on user-configured settings previously set by the user. Additionally or alternatively, in some embodiments, process 300 may determine the blood pressure is to be directly requested via user input responsive to determining there is no communication network available to the wearable device or to a mobile device paired with the wearable device at the current time, that an application for communication with a medical records server is not installed on and/or set up on the wearable device and/or a mobile device paired with the wearable device, or any combination thereof.

Figure 4:
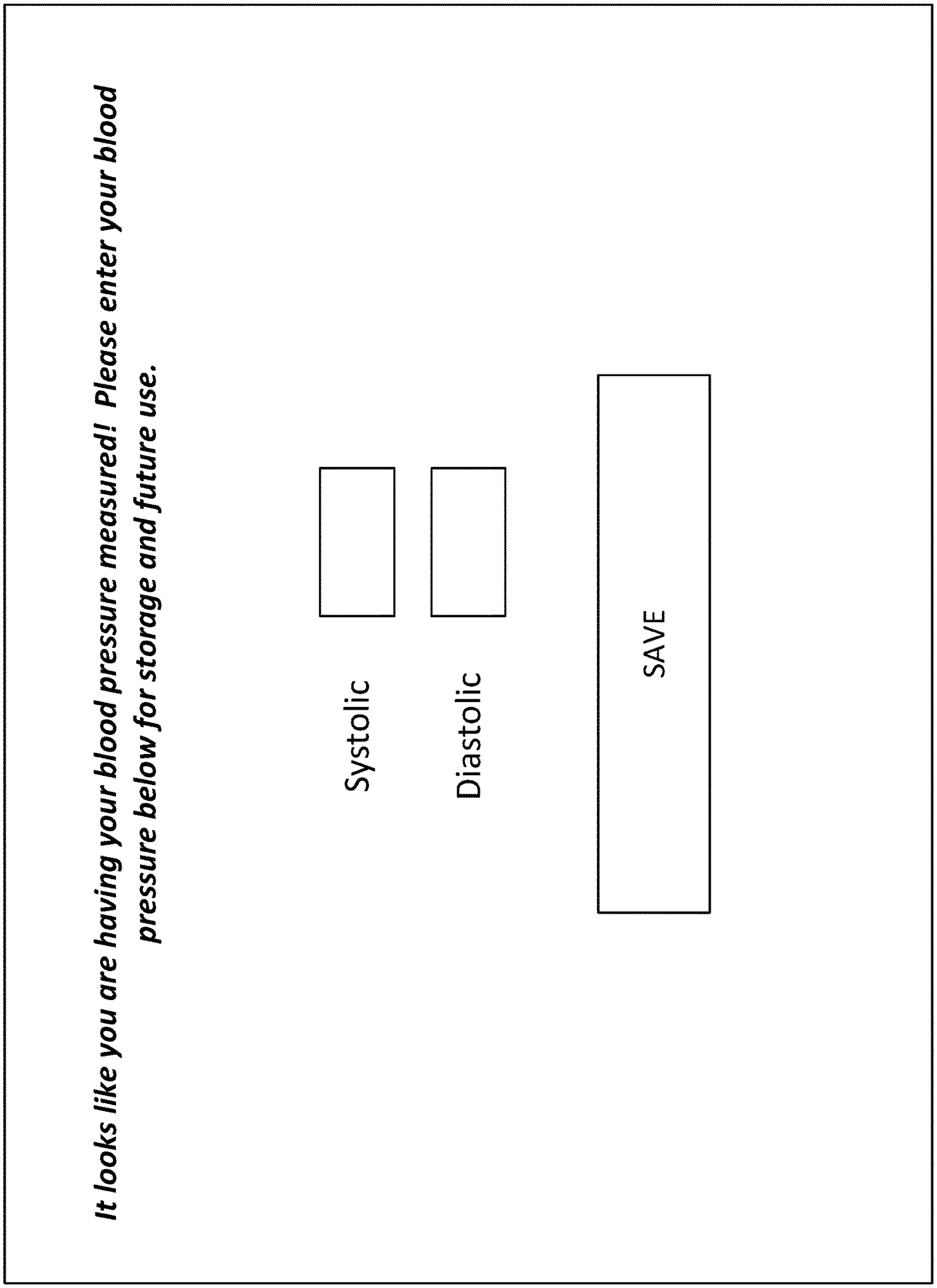
FIG. 4 is an example of a user interface for prompting a user to enter a blood pressure measurement in accordance with some embodiments.

If, at 304, process 300 determines that the blood pressure is to be requested directly from the user ("yes" at 304), process 300 can proceed to block 306 and can provide a user interface configured to receive user input of the blood pressure. The user interface may be presented on the wearable device and/or on a mobile device (e.g., a mobile phone and/or a tablet computer) currently paired with the wearable device, e.g., via a BLUETOOTH connection. An example of such a user interface is shown in FIG. 4. For example, as illustrated in FIG. 4, the user interface may include a message indicating that a determination that the user's blood pressure is being measured has been made. The user interface may include text input boxes and/or drop-down boxes configured to receive explicit user input indicating the systolic blood pressure and/or the diastolic blood pressure.

Referring back to FIG. 3, after obtaining the blood pressure via the user interface, process 300 can proceed to 312, and can store the obtained blood pressure. As described above in connection with block 208 of FIG. 2, the stored blood pressure may be used by the wearable device to calibrate relative blood pressure measurements, or the like.

Conversely, if, at 304, process 300 determines that the blood pressure is not to be requested directly from the user ("no" at 304), process 300 can cause a query of a medical record including the blood pressure measurement to be transmitted to a medical records server based on the time point associated with the PPG signals. For example, the medical records server may be one associated with a particular doctor's office, group of doctor's offices, medical practice, pharmacy, etc. In some implementations, the query may be transmitted using an application programming interface (API) associated with the medical records server. In some embodiments, the query may be transmitted by the wearable device and/or via a mobile device (e.g., a mobile phone, a tablet computer, etc.) paired with the wearable device. In some embodiments, the query may be transmitted responsive to a user confirming (e.g., via an application associated with the medical records server executing on the wearable device and/or a mobile device paired with the wearable device) that the query is to be transmitted. In some embodiments, transmittal of such a query may require the wearable device and/or a mobile device paired with the wearable device being authenticated to the medical records server, e.g., via an application executing on the wearable device and/or a mobile device paired with the wearable device.

In some embodiments, the query may include timing information that may be used by the medical records server to identify the blood pressure measurement. For example, the timing information may include a date and/or a timestamp that indicates a time range during which the blood pressure measurement was taken and/or is to be retrieved from the medical records server. The timestamp may correspond to a timestamp at which it was determined the user's blood pressure was being measured (e.g., as described above at block 204 of FIG. 2) and/or a time at which the PPG signals used to determine the user's blood pressure was being measured were obtained.

At 310, process 300 can receive a blood pressure measurement responsive to the query. Note that, the blood pressure measurement may be received at the device that transmitted the query. For example, in an instance in which the wearable device transmitted the query, the blood pressure measurement may be received at the wearable device. As another example, in an instance in which a mobile device paired with the wearable device transmitted the query, the blood pressure measurement may be received at the mobile device.

After obtaining the blood pressure measurement, process 300 can proceed to 312, and can store the obtained blood pressure. Similar to what is described above, the stored blood pressure may be used by the wearable device to calibrate relative blood pressure measurements, or the like.

Figure 5:
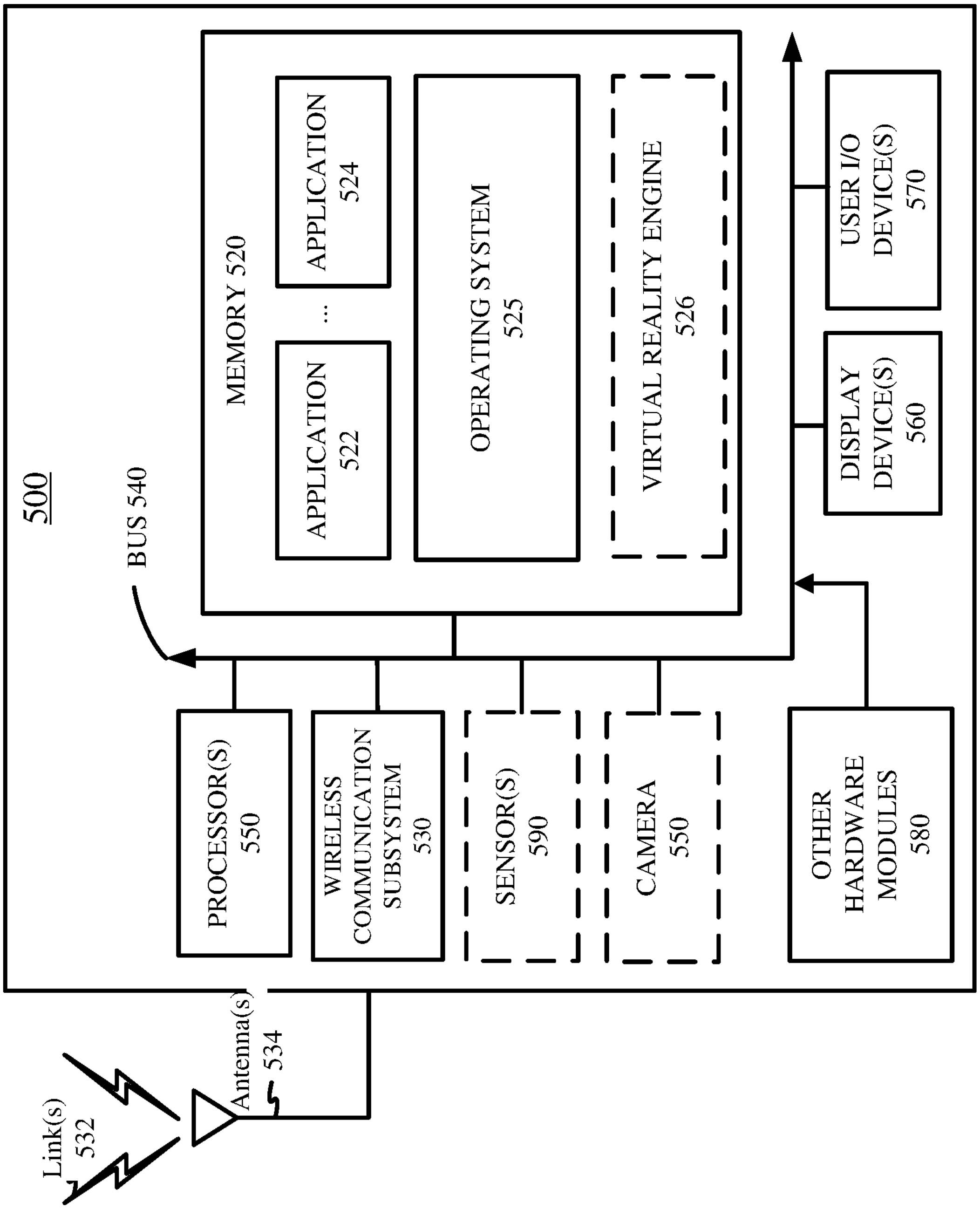
FIG. 5 is a simplified block diagram of an example of a computing system that may be implemented as part of a user device according to certain embodiments.

FIG. 5 is a simplified block diagram of an example of a computing system 500 for implementing some of the examples described herein. For example, computing system 500 may correspond to a computing system associated with a wearable device, as described above in connection with FIGS. 2 and/or 3, a mobile device associated with a wearable device, smart glasses or a headset associated with a wearable device, or the like. In the illustrated example, computing system 500 may include one or more processor(s) 510 and a memory 520. Processor(s) 510 may be configured to execute instructions for performing operations at a number of components, and can be, for example, a general-purpose processor or microprocessor suitable for implementation within a portable electronic device, a wearable device (e.g., a smart watch, a fitness tracker, an AR/VR headset or controller, etc.), a mobile device (e.g., a mobile phone, a tablet computer, etc.). Processor(s) 510 may be communicatively coupled with a plurality of components within computing system 500. To realize this communicative coupling, processor(s) 510 may communicate with the other illustrated components across a bus 540. Bus 540 may be any subsystem adapted to transfer data within computing system 500. Bus 540 may include a plurality of computer buses and additional circuitry to transfer data.

Memory 520 may be coupled to processor(s) 510. In some embodiments, memory 520 may offer both short-term and long-term storage and may be divided into several units. Memory 520 may be volatile, such as static random access memory (SRAM) and/or dynamic random access memory (DRAM) and/or non-volatile, such as read-only memory (ROM), flash memory, and the like. Furthermore, memory 520 may include removable storage devices, such as secure digital (SD) cards. Memory 520 may provide storage of computer-readable instructions, data structures, program modules, and other data for computing system 500. In some embodiments, memory 520 may be distributed into different hardware modules. A set of instructions and/or code might be stored on memory 520. The instructions might take the form of executable code that may be executable by computing system 500, and/or might take the form of source and/or installable code, which, upon compilation and/or installation on computing system 500 (e.g., using any of a variety of generally available compilers, installation programs, compression/decompression utilities, etc.), may take the form of executable code.

In some embodiments, memory 520 may store a plurality of application modules 522 through 524, which may include any number of applications. Examples of applications may include gaming applications, conferencing applications, video playback applications, or other suitable applications. The applications may include a depth sensing function or eye tracking function. Application modules 522-524 may include particular instructions to be executed by processor(s) 510. In some embodiments, certain applications or parts of application modules 522-524 may be executable by other hardware modules 580. In certain embodiments, memory 520 may additionally include secure memory, which may include additional security controls to prevent copying or other unauthorized access to secure information.

In some embodiments, memory 520 may include an operating system 525 loaded therein. Operating system 525 may be operable to initiate the execution of the instructions provided by application modules 522-524 and/or manage other hardware modules 580 as well as interfaces with a wireless communication subsystem 530 which may include one or more wireless transceivers. Operating system 525 may be adapted to perform other operations across the components of computing system 500 including threading, resource management, data storage control and other similar functionality.

Wireless communication subsystem 530 may include, for example, an infrared communication device, a wireless communication device and/or chipset (such as a Bluetooth® device, an IEEE 802.11 device, a Wi-Fi device, a WiMax device, cellular communication facilities, etc.), and/or similar communication interfaces. Computing system 500 may include one or more antennas 534 for wireless communication as part of wireless communication subsystem 530 or as a separate component coupled to any portion of the system. Depending on desired functionality, wireless communication subsystem 530 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 802.17) network. A WLAN may be, for example, an IEEE 802.11x network. A WPAN may be, for example, a Bluetooth network, an IEEE 802.7x, or some other types of network. The techniques described herein may also be used for any combination of WWAN, WLAN, and/or WPAN. Wireless communications subsystem 530 may permit data to be exchanged with a network, other computer systems, and/or any other devices described herein. Wireless communication subsystem 530 may include a means for transmitting or receiving data, such as identifiers of HMD devices, position data, a geographic map, a heat map, photos, or videos, using antenna(s) 534 and wireless link(s) 532. Wireless communication subsystem 530, processor(s) 510, and memory 520 may together comprise at least a part of one or more of a means for performing some functions disclosed herein.

Embodiments of computing system 500 may also include one or more sensors 590. Sensor(s) 590 may include, for example, an image sensor, an accelerometer, a force sensor, a hydrostatic pressure sensor, a temperature sensor, a proximity sensor, a magnetometer, a gyroscope, an inertial sensor (e.g., a module that combines an accelerometer and a gyroscope), an ambient light sensor, or any other similar module operable to provide sensory output and/or receive sensory input, such as a depth sensor or a position sensor. For example, in some implementations, sensor(s) 590 may include one or more inertial measurement units (IMUs) and/or one or more position sensors. An IMU may generate calibration data indicating an estimated position of a device, based on measurement signals received from one or more of the position sensors. A position sensor may generate one or more measurement signals in response to motion of a device. Examples of the position sensors may include, but are not limited to, one or more accelerometers, one or more gyroscopes, one or more magnetometers, another suitable type of sensor that detects motion, a type of sensor used for error correction of the IMU, or some combination thereof. The position sensors may be located external to the IMU, internal to the IMU, or some combination thereof. At least some sensors may use a structured light pattern for sensing.

Computing system 500 may include a display module 560. Display module 560 may be a near-eye display, and may graphically present information, such as images, videos, and various instructions, from computing system 500 to a user. Such information may be derived from one or more application modules 522-524, virtual reality engine 526, one or more other hardware modules 580, a combination thereof, or any other suitable means for resolving graphical content for the user (e.g., by operating system 525). Display module 560 may use liquid crystal display (LCD) technology, light-emitting diode (LED) technology (including, for example, OLED, ILED, μLED, AMOLED, TOLED, etc.), light emitting polymer display (LPD) technology, or some other display technology.

Computing system 500 may include a user input/output module 570. User input/output module 570 may allow a user to send action requests to computing system 500. An action request may be a request to perform a particular action. For example, an action request may be to start or end an application or to perform a particular action within the application. User input/output module 570 may include one or more input devices. Example input devices may include a touchscreen, a touch pad, microphone(s), button(s), dial(s), switch(es), a keyboard, a mouse, a game controller, or any other suitable device for receiving action requests and communicating the received action requests to computing system 500. In some embodiments, user input/output module 570 may provide haptic feedback to the user in accordance with instructions received from computing system 500. For example, the haptic feedback may be provided when an action request is received or has been performed.

Computing system 500 may include a camera 550 that may be used to take photos or videos. Camera 550 may be configured to take photos or videos of the user. Camera 550 may also be used to take photos or videos of the environment, for example, for VR, AR, or MR applications. Camera 550 may include, for example, a complementary metal-oxide-semiconductor (CMOS) image sensor with a few millions or tens of millions of pixels. In some implementations, camera 550 may include two or more cameras that may be used to capture 3-D images.

In some embodiments, computing system 500 may include a plurality of other hardware modules 580. Each of other hardware modules 580 may be a physical module within computing system 500. While each of other hardware modules 580 may be permanently configured as a structure, some of other hardware modules 580 may be temporarily configured to perform specific functions or temporarily activated. Examples of other hardware modules 580 may include, for example, an audio output and/or input module (e.g., a microphone or speaker), a near field communication (NFC) module, a rechargeable battery, a battery management system, a wired/wireless battery charging system, etc. In some embodiments, one or more functions of other hardware modules 580 may be implemented in software.

In some embodiments, memory 520 of computing system 500 may also store a virtual reality engine 526. Virtual reality engine 526 may execute applications within computing system 500 and receive position information, acceleration information, velocity information, predicted future positions, or some combination thereof from the various sensors. In some embodiments, the information received by virtual reality engine 526 may be used for producing a signal (e.g., display instructions) to display module 560. For example, if the received information indicates that the user has looked to the left, virtual reality engine 526 may generate content that mirrors the user's movement in a virtual environment. Additionally, virtual reality engine 526 may perform an action within an application in response to an action request received from user input/output module 570 and provide feedback to the user. The provided feedback may be visual, audible, or haptic feedback. In some implementations, processor(s) 510 may include one or more GPUs that may execute virtual reality engine 526.

In various implementations, the above-described hardware and modules may be implemented on a single device or on multiple devices that can communicate with one another using wired or wireless connections. For example, in some implementations, some components or modules, such as GPUs, virtual reality engine 526, and applications (e.g., tracking application), may be implemented on two or more paired or connected devices.

In alternative configurations, different and/or additional components may be included in computing system 500. Similarly, functionality of one or more of the components can be distributed among the components in a manner different from the manner described above. For example, in some embodiments, computing system 500 may be modified to include other system environments, such as an AR system environment and/or an MR environment.

Figure 6:
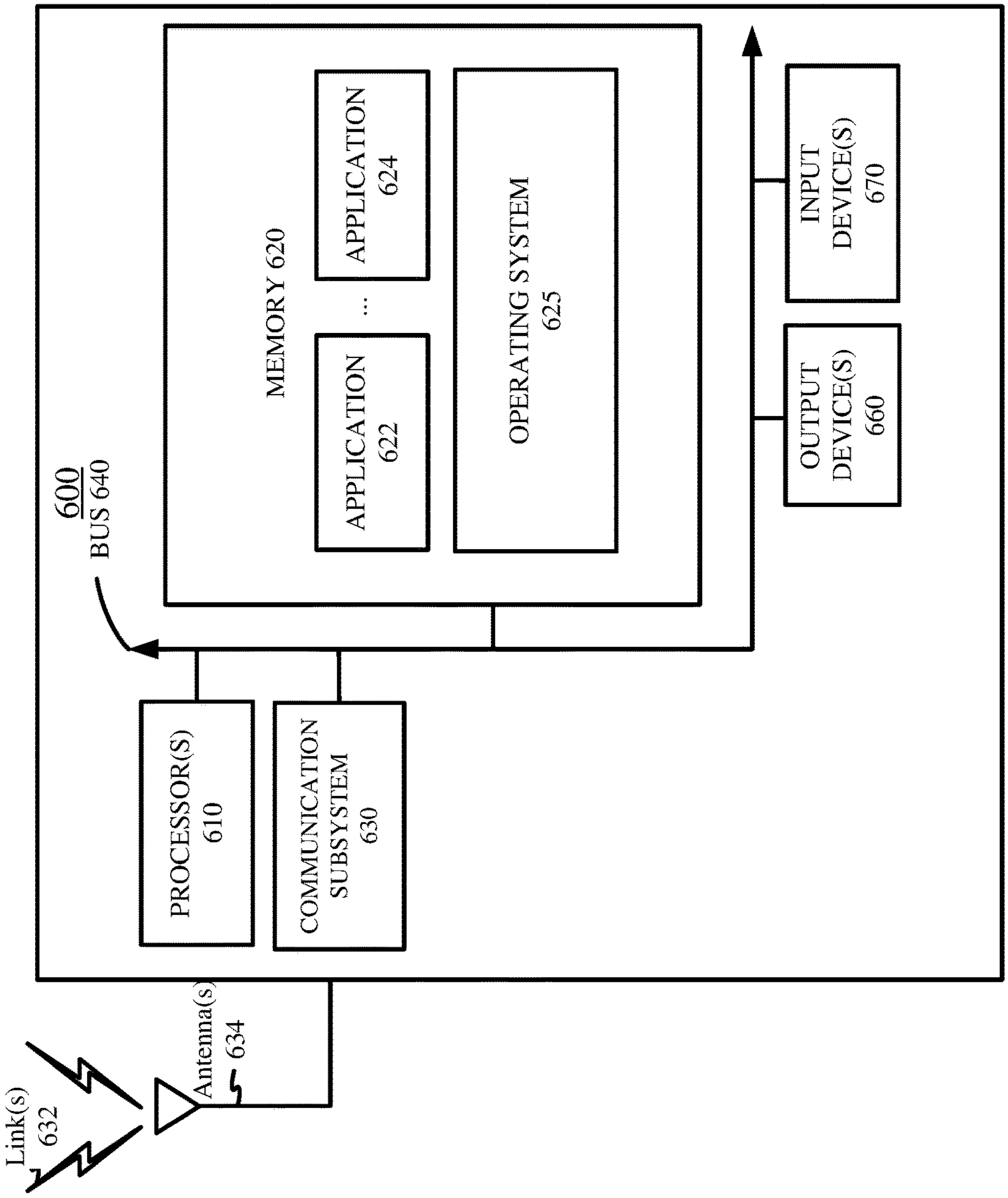
FIG. 6 is a simplified block diagram of an example of a computing system that may be implemented as part of a server according to certain embodiments.

FIG. 6 is a simplified block diagram of an example of a computing system 600 that may be implemented in connection with a server in accordance with some embodiments. For example, computing system 600 may be used to implement a server used to generate and/or train various machine learning models, store medical records, or the like. For example, computing system 600 may be associated with a medical records server that receives a query as described above in connection with FIG. 3.

In the illustrated example, computing system 600 may include one or more processor(s) 610 and a memory 620. Processor(s) 610 may be configured to execute instructions for performing operations at a number of components, and can be, for example, a general-purpose processor or microprocessor suitable for implementation within a server device. Processor(s) 610 may be communicatively coupled with a plurality of components within computing system 600. To realize this communicative coupling, processor(s) 610 may communicate with the other illustrated components across a bus 640. Bus 640 may be any subsystem adapted to transfer data within computing system 600. Bus 640 may include a plurality of computer buses and additional circuitry to transfer data.

Memory 620 may be coupled to processor(s) 610. In some embodiments, memory 620 may offer both short-term and long-term storage and may be divided into several units. Memory 620 may be volatile, such as static random access memory (SRAM) and/or dynamic random access memory (DRAM) and/or non-volatile, such as read-only memory (ROM), flash memory, and the like. Furthermore, memory 620 may include removable storage devices, such as secure digital (SD) cards. Memory 620 may provide storage of computer-readable instructions, data structures, program modules, and other data for computing system 600. In some embodiments, memory 620 may be distributed into different hardware modules. A set of instructions and/or code might be stored on memory 620. The instructions might take the form of executable code that may be executable by computing system 600, and/or might take the form of source and/or installable code, which, upon compilation and/or installation on computing system 600 (e.g., using any of a variety of generally available compilers, installation programs, compression/decompression utilities, etc.), may take the form of executable code.

In some embodiments, memory 620 may store a plurality of application modules 622 through 624, which may include any number of applications. Examples of applications may include gaming applications, conferencing applications, video playback applications, or other suitable applications. Application modules 622-624 may include particular instructions to be executed by processor(s) 610. In some embodiments, certain applications or parts of application modules 622-624 may be executable by other hardware modules. In certain embodiments, memory 620 may additionally include secure memory, which may include additional security controls to prevent copying or other unauthorized access to secure information.

In some embodiments, memory 620 may include an operating system 625 loaded therein. Operating system 625 may be operable to initiate the execution of the instructions provided by application modules 622-624 and/or manage other hardware modules as well as interfaces with a wireless communication subsystem 630 which may include one or more wireless transceivers. Operating system 625 may be adapted to perform other operations across the components of computing system 600 including threading, resource management, data storage control and other similar functionality.

Communication subsystem 630 may include, for example, an infrared communication device, a wireless communication device and/or chipset (such as a Bluetooth® device, an IEEE 802.11 device, a Wi-Fi device, a WiMax device, cellular communication facilities, etc.), a wired communication interface, and/or similar communication interfaces. Computing system 600 may include one or more antennas 634 for wireless communication as part of wireless communication subsystem 630 or as a separate component coupled to any portion of the system. Depending on desired functionality, communication subsystem 630 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 802.17) network. A WLAN may be, for example, an IEEE 802.11x network. A WPAN may be, for example, a Bluetooth network, an IEEE 802.8x, or some other types of network. The techniques described herein may also be used for any combination of WWAN, WLAN, and/or WPAN. Communications subsystem 630 may permit data to be exchanged with a network, other computer systems, and/or any other devices described herein. Communication subsystem 630 may include a means for transmitting or receiving data, using antenna(s) 634, wireless link(s) 632, or a wired link. Communication subsystem 630, processor(s) 610, and memory 620 may together comprise at least a part of one or more of a means for performing some functions disclosed herein.

In some embodiments, computing system 600 may include one or more output device(s) 660 and/or one or more input device(s) 670. Output device(s) 670 and/or input device(s) 670 may be used to provide output information and/or receive input information.

Embodiments disclosed herein may be used to implement components of an artificial reality system or may be implemented in conjunction with an artificial reality system. Artificial reality is a form of reality that has been adjusted in some manner before presentation to a user, which may include, for example, a virtual reality, an augmented reality, a mixed reality, a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, for example, create content in an artificial reality and/or are otherwise used in (e.g., perform activities in) an artificial reality. The artificial reality system that provides the artificial reality content may be implemented on various platforms, including an HMD connected to a host computer system, a standalone HMD, a mobile device or computing system, or any other hardware platform capable of providing artificial reality content to one or more viewers.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Specific details are given in the description to provide a thorough understanding of the embodiments. However, embodiments may be practiced without these specific details. For example, well-known circuits, processes, systems, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing various embodiments. Various changes may be made in the function and arrangement of elements without departing from the spirit and scope of the present disclosure.

Also, some embodiments were described as processes depicted as flow diagrams or block diagrams. Although each may describe the operations as a sequential process, many of the operations may be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It will be apparent to those skilled in the art that substantial variations may be made in accordance with specific requirements. For example, customized or special-purpose hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The term "machine-readable medium" and "computer-readable medium" may refer to any storage medium that participates in providing data that causes a machine to operate in a specific fashion. In embodiments provided hereinabove, various machine-readable media might be involved in providing instructions/code to processing units and/or other device(s) for execution. Additionally or alternatively, the machine-readable media might be used to store and/or carry such instructions/code. In many implementations, a computer-readable medium is a physical and/or tangible storage medium. Such a medium may take many forms, including, but not limited to, non-volatile media, volatile media, and transmission media. Common forms of computer-readable media include, for example, magnetic and/or optical media such as compact disk (CD) or digital versatile disk (DVD), punch cards, paper tape, any other physical medium with patterns of holes, a RAM, a programmable read-only memory (PROM), an erasable programmable read-only memory (EPROM), a FLASH-EPROM, any other memory chip or cartridge, a carrier wave as described hereinafter, or any other medium from which a computer can read instructions and/or code. A computer program product may include code and/or machine-executable instructions that may represent a procedure, a function, a subprogram, a program, a routine, an application (App), a subroutine, a module, a software package, a class, or any combination of instructions, data structures, or program statements.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and" and "or" as used herein, may include a variety of meanings that are also expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AC, BC, AA, ABC, AAB, AABBCCC, etc.

Further, while certain embodiments have been described using a particular combination of hardware and software, it should be recognized that other combinations of hardware and software are also possible. Certain embodiments may be implemented only in hardware, or only in software, or using combinations thereof. In one example, software may be implemented with a computer program product containing computer program code or instructions executable by one or more processors for performing any or all of the steps, operations, or processes described in this disclosure, where the computer program may be stored on a non-transitory computer readable medium. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques, including, but not limited to, conventional techniques for inter-process communications, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific embodiments have been described, these are not intended to be limiting. Various modifications and equivalents are within the scope of the following claims.

Example Embodiments

Embodiment 1. A method for detecting blood pressure measurements, the method comprising: obtaining a set of photoplethysmography (PPG) signals using a wearable device worn by a user; determining that a blood pressure of the user is being measured by a device unassociated with the wearable device based at least in part on the set of PPG signals; responsive to determining that the blood pressure of the user is being measured by the device unassociated with the wearable device, obtaining an indication of a blood pressure measurement obtained by the device unassociated with the wearable device; and storing the obtained indication of the blood pressure measurement for future use by the wearable device.

Embodiment 2. The method of embodiment 1, wherein the device unassociated with the wearable device comprises an inflatable cuff.

Embodiment 3. The method of any one of embodiments 1 or 2, wherein the device unassociated with the wearable device is not communicatively coupled to the wearable device or a mobile device paired with the wearable device.

Embodiment 4. The method of any one of embodiments 1-3, wherein determining that the blood pressure of the user is being measured comprises detecting a characteristic of an occlusion of arterial blood vessels during a portion of a time the blood pressure is being measured based at least in part on the set of PPG signals.

Embodiment 5. The method of embodiment 4, wherein the characteristic of the occlusion of the arterial blood vessels comprises a change in an amplitude of a portion of the set of PPG signals that exceeds a change threshold.

Embodiment 6. The method of embodiment 4, wherein the characteristic of the occlusion of the arterial blood vessels comprises an amplitude of a portion of the set of PPG signals being below a predetermined threshold.

Embodiment 7. The method of any one of embodiments 1-6, wherein determining that the blood pressure of the user is being measured comprises determining an arm position of an arm of the user based at least in part on one or more motion sensors of the wearable device.

Embodiment 8. The method of embodiment 7, wherein determining that the blood pressure of the user is being measured comprises determining that the arm position is one of a set of possible blood pressure measurement arm positions.

Embodiment 9. The method of any one of embodiments 1-8, wherein obtaining the indication of the blood pressure measurement comprises causing a user interface to be presented, wherein the user interface is configured to receive a user input corresponding to the indication of the blood pressure measurement.

Embodiment 10. The method of embodiment 9, wherein the user interface is presented on at least one of: the wearable device; a mobile phone paired with the wearable device; or a second wearable device paired with the wearable device.

Embodiment 11. The method of any one of embodiments 1-10, wherein obtaining the indication of the blood pressure measurement comprises causing a query to be transmitted to a medical records server, wherein the query requests the indication of the blood pressure measurement.

Embodiment 12. The method of embodiment 11, wherein the query is transmitted by a mobile device paired with the wearable device.

Embodiment 13. The method of embodiment 11, wherein the query is transmitted using an application programming interface (API) associated with the medical records server.

Embodiment 14. The method of any one of embodiments 11-13, wherein the query comprises timing information corresponding to a time point at which the set of PPG signals were obtained.

Embodiment 15. A wearable device, comprising: at least one light emitter and at least one light detector; and a controller configured to: obtain a set of photoplethysmography (PPG) signals using the at least one light emitter and at least one light detector; determine that a blood pressure of a user wearing the wearable device is being measured by a device unassociated with the wearable device based at least in part on the set of PPG signals; responsive to determining that the blood pressure of the user is being measured by the device unassociated with the wearable device, obtain an indication of a blood pressure measurement obtained by the device unassociated with the wearable device; and store the obtained indication of the blood pressure measurement for future use by the wearable device.

Embodiment 16. The wearable device of embodiment 15, wherein the wearable device is paired with a mobile device, and wherein obtaining the indication of the blood pressure measurement is via the mobile device.

Embodiment 17. The wearable device of any one of embodiments 15 or 16, wherein obtaining the indication of the blood pressure measurement comprises causing a user interface to be presented, wherein the user interface is configured to receive user input specifying the indication of the blood pressure measurement.

Embodiment 18. The wearable device of any one of embodiments 15-18, wherein obtaining the indication of the blood pressure measurement comprises causing a query requesting the indication of the blood pressure measurement to be transmitted to a medical records server.

Embodiment 19. The wearable device of any one of embodiments 15-19, wherein determining that the blood pressure of the user is being measured comprises determining an arm position of the user.

Embodiment 20. The wearable device of embodiment 19, wherein determining the arm position of the user is based on at least one of: one or more motion sensors of the wearable device; electromyography (EMG) signals obtained using one or more electrodes disposed in or on a portion of the wearable device Embodiment 21. A method for detecting blood pressure measurements, the method comprising: obtaining a set of photoplethysmography (PPG) signals using a wearable device worn by a user; determining that a blood pressure of the user is being measured by another device, based at least in part on the set of PPG signals and without communicating any data to or from the other device; responsive to determining that the blood pressure of the user is being measured by the another device, obtaining an indication of a blood pressure measurement obtained by the another device; and storing the obtained indication of the blood pressure measurement for future use by the wearable device.

What is claimed is:

1. A method for detecting blood pressure measurements, the method comprising:
- obtaining a set of photoplethysmography (PPG) signals using a wearable device worn by a user;
- determining that a blood pressure of the user is being measured by a device unassociated with the wearable device based at least in part on the set of PPG signals;
- responsive to determining that the blood pressure of the user is being measured by the device unassociated with the wearable device, obtaining an indication of a blood pressure measurement obtained by the device unassociated with the wearable device; and
- storing the obtained indication of the blood pressure measurement for use in calibrating blood pressure measurements obtained by the wearable device.

2. The method of claim 1, wherein the device unassociated with the wearable device comprises an inflatable cuff.

3. The method of claim 1, wherein the device unassociated with the wearable device is not communicatively coupled to the wearable device or a mobile device paired with the wearable device.

4. The method of claim 1, wherein determining that the blood pressure of the user is being measured comprises detecting a characteristic of an occlusion of arterial blood vessels during a portion of a time the blood pressure is being measured based at least in part on the set of PPG signals.

5. The method of claim 4, wherein the characteristic of the occlusion of the arterial blood vessels comprises a change in an amplitude of a portion of the set of PPG signals that exceeds a change threshold.

6. The method of claim 4, wherein the characteristic of the occlusion of the arterial blood vessels comprises an amplitude of a portion of the set of PPG signals being below a predetermined threshold.

7. The method of claim 1, wherein determining that the blood pressure of the user is being measured comprises determining an arm position of an arm of the user based at least in part on one or more motion sensors of the wearable device.

8. The method of claim 7, wherein determining that the blood pressure of the user is being measured comprises determining that the arm position is one of a set of possible blood pressure measurement arm positions.

9. The method of claim 1, wherein obtaining the indication of the blood pressure measurement comprises causing a user interface to be presented, wherein the user interface is configured to receive a user input corresponding to the indication of the blood pressure measurement.

10. The method of claim 9, wherein the user interface is presented on at least one of: the wearable device; a mobile phone paired with the wearable device; or a second wearable device paired with the wearable device.

11. The method of claim 1, wherein obtaining the indication of the blood pressure measurement comprises causing a query to be transmitted to a medical records server, wherein the query requests the indication of the blood pressure measurement.

12. The method of claim 11, wherein the query is transmitted by a mobile device paired with the wearable device.

13. The method of claim 11, wherein the query is transmitted using an application programming interface (API) associated with the medical records server.

14. The method of claim 11, wherein the query comprises timing information corresponding to a time point at which the set of PPG signals was obtained.

15. A wearable device, comprising:

at least one light emitter and at least one light detector; and a controller configured to:

obtain a set of photoplethysmography (PPG) signals using the at least one light emitter and the at least one light detector;

determine that a blood pressure of a user wearing the wearable device is being measured by a device unassociated with the wearable device based at least in part on the set of PPG signals;

responsive to determining that the blood pressure of the user is being measured by the device unassociated with the wearable device, obtain an indication of a blood pressure measurement obtained by the device unassociated with the wearable device; and store the obtained indication of the blood pressure measurement for use in calibrating blood pressure measurements obtained by the wearable device.

16. The wearable device of claim 15, wherein the wearable device is paired with a mobile device, and wherein obtaining the indication of the blood pressure measurement is via the mobile device.

17. The wearable device of claim 15, wherein obtaining the indication of the blood pressure measurement comprises causing a user interface to be presented, wherein the user interface is configured to receive user input specifying the indication of the blood pressure measurement.

18. The wearable device of claim 15, wherein obtaining the indication of the blood pressure measurement comprises causing a query requesting the indication of the blood pressure measurement to be transmitted to a medical records server.

19. The wearable device of claim 15, wherein determining that the blood pressure of the user is being measured comprises determining an arm position of the user.

20. The wearable device of claim 19, wherein determining the arm position of the user is based on at least one of:

one or more motion sensors of the wearable device; and electromyography (EMG) signals obtained using one or more electrodes disposed in or on a portion of the wearable device.

* * * * *